(12) United States Patent
Barbagli et al.

(10) Patent No.: US 11,832,891 B2
(45) Date of Patent: Dec. 5, 2023

(54) SYSTEMS AND METHODS FOR FAULT REACTION MECHANISMS FOR MEDICAL ROBOTIC SYSTEMS

(71) Applicant: INTUITIVE SURGICAL OPERATIONS, INC., Sunnyvale, CA (US)

(72) Inventors: Federico Barbagli, San Francisco, CA (US); Christopher R. Carlson, Belmont, CA (US); Samuel Y. Chang, Mountain View, CA (US); Nicola Diolaiti, Menlo Park, CA (US); Vincent Duindam, San Francisco, CA (US); Salomon J. Trujillo, Fremont, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 1140 days.

(21) Appl. No.: 16/306,418

(22) PCT Filed: Jun. 30, 2017

(86) PCT No.: PCT/US2017/040438
§ 371 (c)(1),
(2) Date: Nov. 30, 2018

(87) PCT Pub. No.: WO2018/006046
PCT Pub. Date: Jan. 4, 2018

(65) Prior Publication Data
US 2020/0078096 A1    Mar. 12, 2020

Related U.S. Application Data

(60) Provisional application No. 62/357,121, filed on Jun. 30, 2016.

(51) Int. Cl.
*A61B 34/20* (2016.01)
*A61B 34/32* (2016.01)
(Continued)

(52) U.S. Cl.
CPC ........ *A61B 34/20* (2016.02); *A61B 17/00234* (2013.01); *A61B 34/25* (2016.02);
(Continued)

(58) Field of Classification Search
CPC ............ A61B 34/20; A61B 2034/2061; A61B 2034/301; A61B 2034/303; A61B 2560/0276
See application file for complete search history.

(56) References Cited

U.S. PATENT DOCUMENTS

| 6,380,732 B1 | 4/2002 | Gilboa |
| 6,389,187 B1 | 5/2002 | Greenaway et al. |

(Continued)

FOREIGN PATENT DOCUMENTS

| CN | 105208949 A | 12/2015 |
| EP | 2584991 A1 | 5/2013 |
| WO | WO-2016032902 A1 | 3/2016 |

OTHER PUBLICATIONS

St. Jude Medical., "OPTIS™ Integrated System Instructions for Use," Apr. 2014, 250 pages.
(Continued)

*Primary Examiner* — Jason M Ip
(74) *Attorney, Agent, or Firm* — HAYNES AND BOONE, LLP

(57) ABSTRACT

A medical robotic system includes a control system and a manipulator assembly including actuators to manipulate a flexible elongate body, including a rotation actuator to bend the flexible elongate body. The control system is configured to perform: determining an operational state of the system; detecting a fault in one or more components of the system; classifying the fault with one or more classifications of a plurality of classifications according to heuristics; and imposing a fault reaction state on the system based on the
(Continued)

classifications to mitigate the fault. The control system is configured to impose a first fault reaction state for a motion actuation fault and impose a second fault reaction state for a non-motion actuation fault. The first fault reaction state includes controlling the rotation actuator to cause the elongate body to become compliant to external forces placed upon the elongate body by walls of an anatomical passageway.

17 Claims, 7 Drawing Sheets

(51) Int. Cl.
| | |
|---|---|
| *A61B 17/00* | (2006.01) |
| *A61B 34/30* | (2016.01) |
| *A61B 34/00* | (2016.01) |
| *A61B 34/35* | (2016.01) |

(52) U.S. Cl.
CPC .............. *A61B 34/32* (2016.02); *A61B 34/35* (2016.02); *A61B 2017/00075* (2013.01); *A61B 2017/00119* (2013.01); *A61B 2017/00809* (2013.01); *A61B 2034/2061* (2016.02); *A61B 2034/301* (2016.02); *A61B 2034/303* (2016.02); *A61B 2560/0276* (2013.01)

(56) References Cited

U.S. PATENT DOCUMENTS

| | | | |
|---|---|---|---|
| 7,316,681 B2 | 1/2008 | Madhani et al. | |
| 7,772,541 B2 | 8/2010 | Froggatt et al. | |
| 8,900,131 B2 | 12/2014 | Chopra et al. | |
| 9,259,274 B2 | 2/2016 | Prisco | |
| 9,452,276 B2 | 9/2016 | Duindam et al. | |
| 2006/0013523 A1 | 1/2006 | Childlers et al. | |
| 2006/0095022 A1* | 5/2006 | Moll | A61B 34/20 606/1 |
| 2007/0112255 A1 | 5/2007 | Ikeda et al. | |
| 2007/0135803 A1* | 6/2007 | Belson | A61B 1/00154 606/1 |
| 2007/0197896 A1 | 8/2007 | Moll et al. | |
| 2008/0177283 A1 | 7/2008 | Lee et al. | |
| 2008/0294144 A1* | 11/2008 | Leo | A61B 5/6885 604/535 |
| 2010/0099951 A1 | 4/2010 | Laby et al. | |
| 2011/0040305 A1* | 2/2011 | Gomez | A61B 34/74 606/130 |
| 2011/0319815 A1 | 12/2011 | Roelle et al. | |
| 2013/0204124 A1 | 8/2013 | Duindam et al. | |
| 2015/0011830 A1 | 1/2015 | Hunter et al. | |
| 2015/0112481 A1* | 4/2015 | Burns | B25J 9/1674 700/248 |
| 2017/0100197 A1* | 4/2017 | Zubiate | A61B 34/37 |

OTHER PUBLICATIONS

International Preliminary Report on Patentability for Application No. PCT/US2017/040438, dated Jan. 10, 2019, 12 pages.
International Search Report and Written Opinion for Application No. PCT/US2017/040438, dated Nov. 15, 2017, 15 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

SYSTEMS AND METHODS FOR FAULT REACTION MECHANISMS FOR MEDICAL ROBOTIC SYSTEMS

RELATED APPLICATIONS

This patent application is the U.S. national phase of International Application No. PCT/US2017/040438, filed Jun. 30, 2017, which designated the U.S. and claims priority to and the benefit of the filing date of U.S. Provisional Patent Application 62/357,121, entitled "SYSTEMS AND METHODS FOR FAULT REACTION MECHANISMS FOR MEDICAL ROBOTIC SYSTEMS," filed Jun. 30, 2016, which are incorporated by reference in their entirety.

FIELD

The present disclosure is directed to systems and methods for reacting to failures in medical robotic systems, and more particularly to systems and methods for handling such failures in medical robotic systems being used in a medical procedure.

BACKGROUND

Minimally invasive surgical techniques using computer-assisted medical devices generally attempt to perform surgical and/or other procedures while minimizing damage to healthy tissue. Some minimally invasive procedures may be performed remotely through the use of computer-assisted medical devices with surgical instruments. With many computer-assisted medical devices, a physician and/or other medical personnel may typically manipulate input devices using one or more controls on an operator console. As the physician and/or other medical personnel operate the various controls at the physician console, the commands are relayed from the physician console to a patient side device to which one or more end effectors and/or surgical instruments are mounted. In this way, the physician and/or other medical personnel are able to perform one or more procedures on a patient using the end effectors and/or surgical instruments. Depending upon the desired procedure and/or the surgical instruments in use, the desired procedure may be performed partially or wholly under control of the physician and/or medical personnel using teleoperation and/or under semi-autonomous control where the surgical instrument may perform a sequence of operations based on one or more activation actions by the physician and/or other medical personnel.

Minimally invasive surgical systems, whether actuated manually, teleoperatively, and/or semi-autonomously may be used in a variety of operations and/or procedures and may have various configurations. Many such systems have instruments that include an end effector mounted at a distal end of a shaft that may be mounted to the distal end of an articulated arm. In many operational scenarios, the shaft may be configured to be inserted (e.g., laparoscopically, thoracoscopically, and/or the like) through an opening (e.g., a body wall incision, a natural orifice, and/or the like) to reach a remote surgical site. In some instruments, an articulating wrist mechanism may be mounted to the distal end of the instrument's shaft to support the end effector with the articulating wrist providing the ability to alter an orientation of the end effector relative to a longitudinal axis of the shaft. The articulating wrist mechanism may be provided by a flexible robotic arm or catheter.

End effectors of different design and/or configuration may be used to perform different tasks, procedures, and functions so as to be allow the physician and/or other medical personnel to perform any of a variety of surgical procedures. Examples include, but are not limited to, cauterizing, ablating, suturing, cutting, stapling, fusing, sealing, etc., and/or combinations thereof. Accordingly, end effectors can include a variety of components and/or combinations of components to perform these surgical procedures. These end effectors may be affixed to a distal end of the flexible robotic catheter or may be delivered to a surgical site through one or more lumens extending along the length of the flexible robotic catheter.

During a surgery using a flexible robotic catheter, when one or more of the components encounters a fault condition while attempting to perform the desired procedure, it may be difficult for the physician and/or other medical personnel to detect and/or correct the fault condition due to the limited visibility of the end effector, the limited space in which the surgical instrument operates, the limited access to the surgical instrument, the remote position of the end effector relative to the physician and/or other medical personnel, and/or the like. Accordingly, improved methods and systems for reacting to fault conditions are desired.

SUMMARY

The embodiments of the invention are best summarized by the claims that follow the description.

However, consistent with some embodiments, a medical robotic system includes a manipulator assembly having one or more actuators configured to manipulate a flexible elongate body and a control system configured to perform operations. The operations include determining an operational state of the medical robotic system, detecting a fault in one or more components of the medical robotic system, classifying the fault according to one or more heuristics, and imposing a fault reaction state on the medical robotic system based on the one or more heuristics to mitigate the fault.

Consistent with some embodiments, a method of controlling a medical robotic system includes operations of determining an operational state of the medical robotic system comprising an elongate body having a proximal end, a distal end, and a lumen therebetween, detecting a fault in one or more components of the medical robotic system, and classifying the fault according to one or more heuristics. Some embodiments of the medium further include instructions for imposing, by a control system, a fault reaction state on the medical robotic system based on the operational state of the medical robotic system and the classification of the fault to mitigate the fault.

Consistent with some embodiments, non-transitory computer-readable storage medium are provide that have instructions stored thereon. When the instructions are executed by one or more processors, such as the processor or processors of a robotic control system perform operations including determining an operational state of the medical robotic system comprising an elongate body having a proximal end, a distal end, and a lumen therebetween, detecting a fault in one or more components of the medical robotic system, and classifying the fault according to one or more heuristics. Some embodiments of the medium further include instructions for imposing, by a control system, a fault reaction state on the medical robotic system based on the operational state of the medical robotic system and the classification of the fault to mitigate the fault.

Embodiments further include causing actuators coupled to the elongate body to maintain a shape of the elongate body, when the operational state indicates that a medical instrument is protruding out from the lumen and causing the actuators to become compliant to external forces placed upon the elongate body by walls of the anatomical passageway of the patient, when the operational state indicates that the medical instrument is not protruding out from the lumen.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

Figure 2:
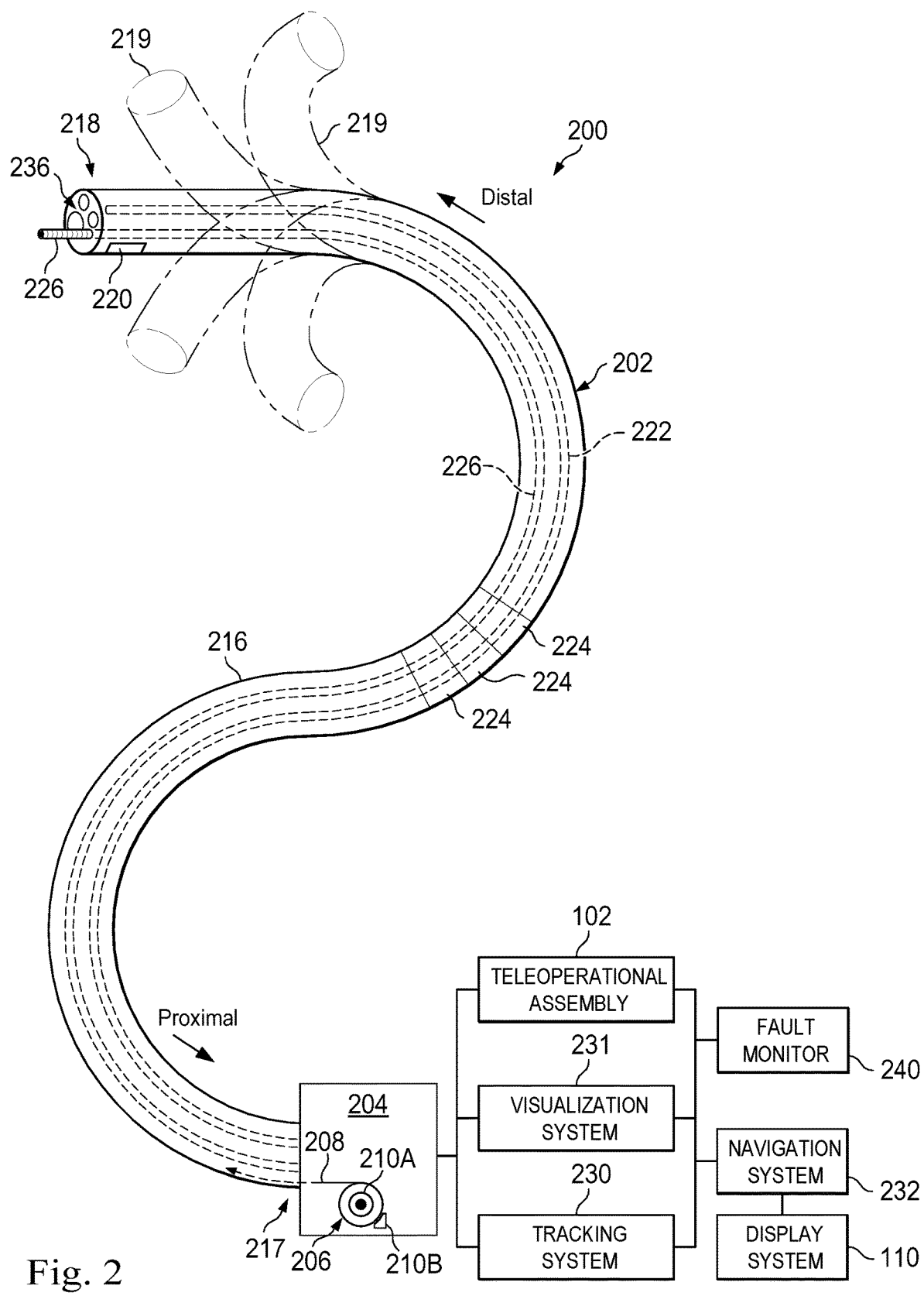
FIG. 2 illustrates a medical robotic system utilizing aspects of the present disclosure.
Figure 3A:
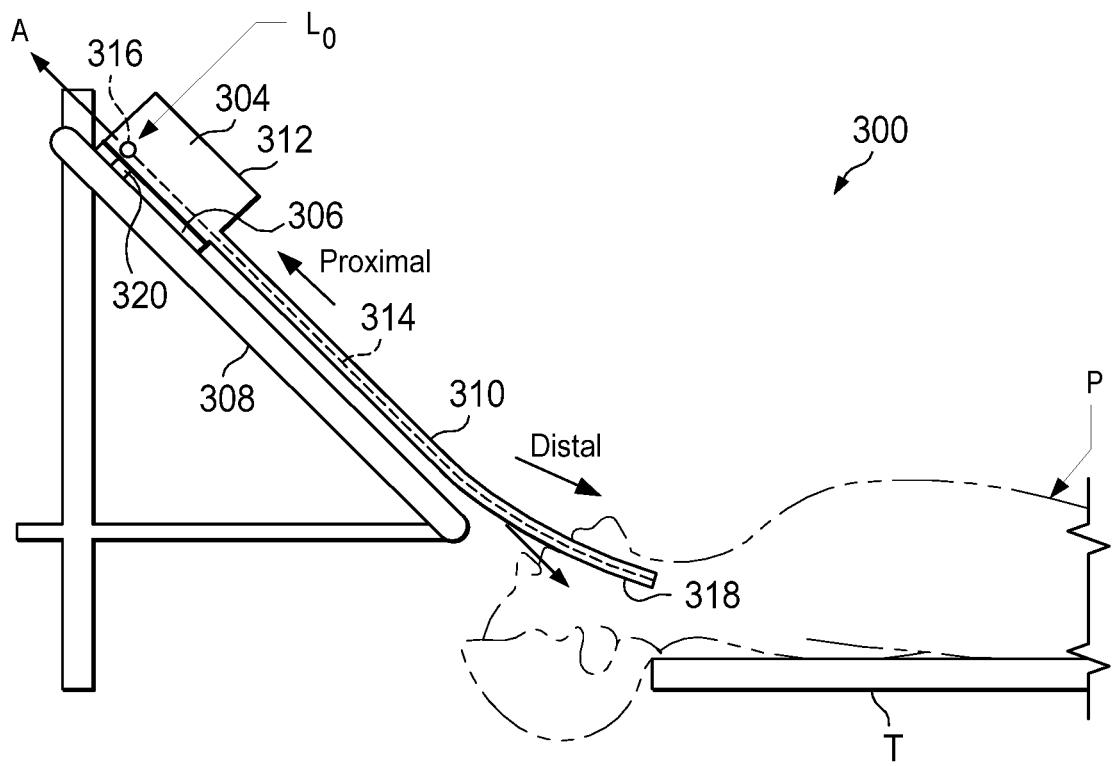
FIGS. 3A and 3B are side views of a patient coordinate space including a flexible medical instrument mounted on an insertion assembly according to an embodiment of the present disclosure.
Figure 3B:
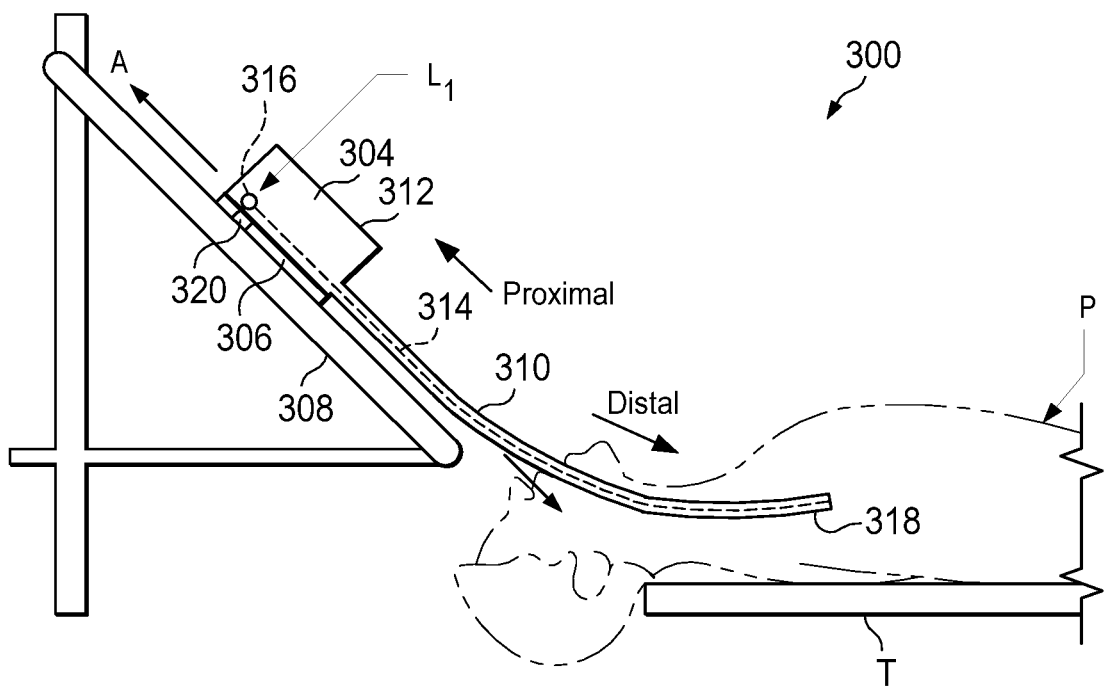
Figure 4A:
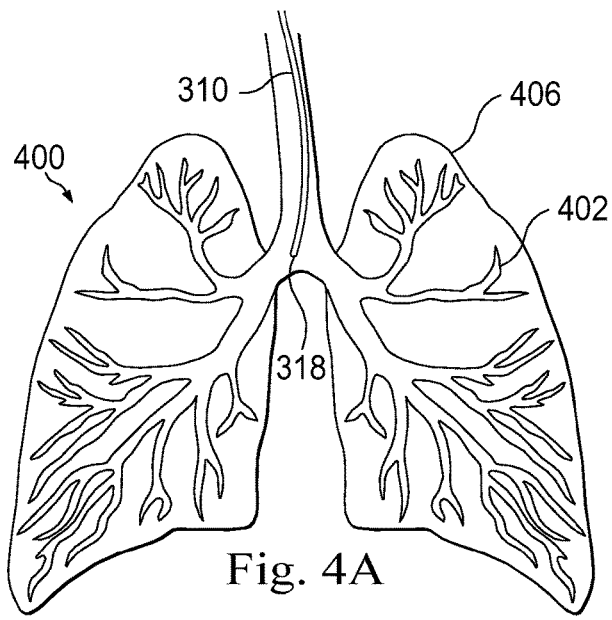
Figure 4B:
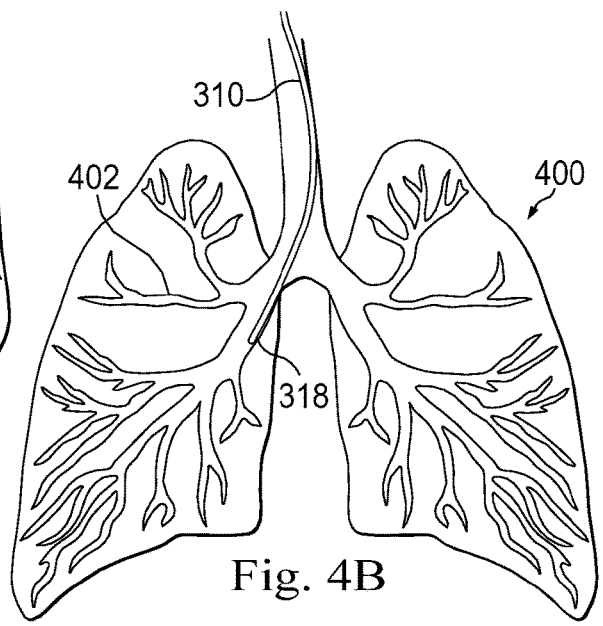
Figure 4C:
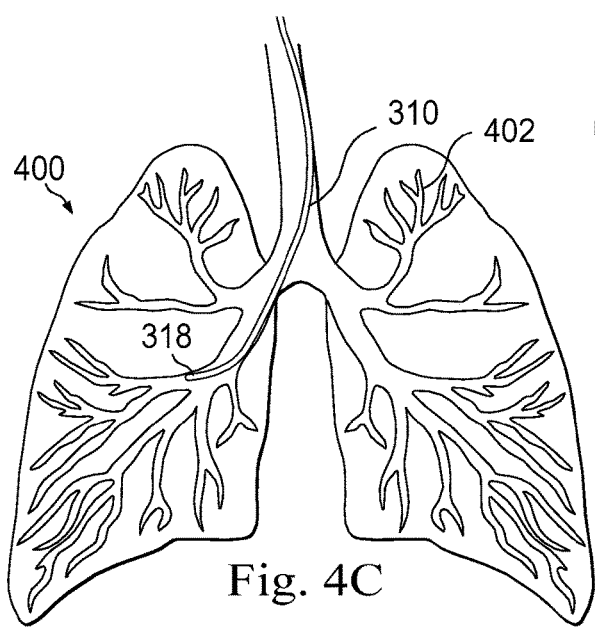
Figure 4D:
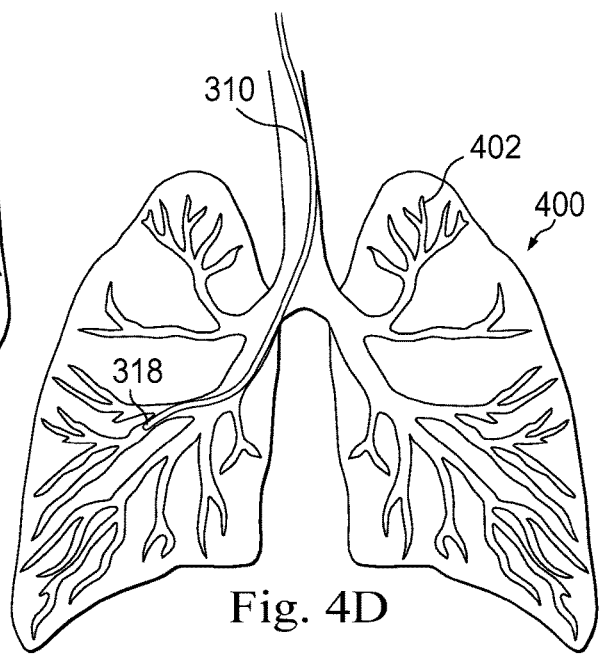

FIGS. 4A, 4B, 4C, and 4D illustrate the distal end of the medical robotic system of FIGS. 2, 3A, and 3B, during insertion within a human lung.

Figure 5:
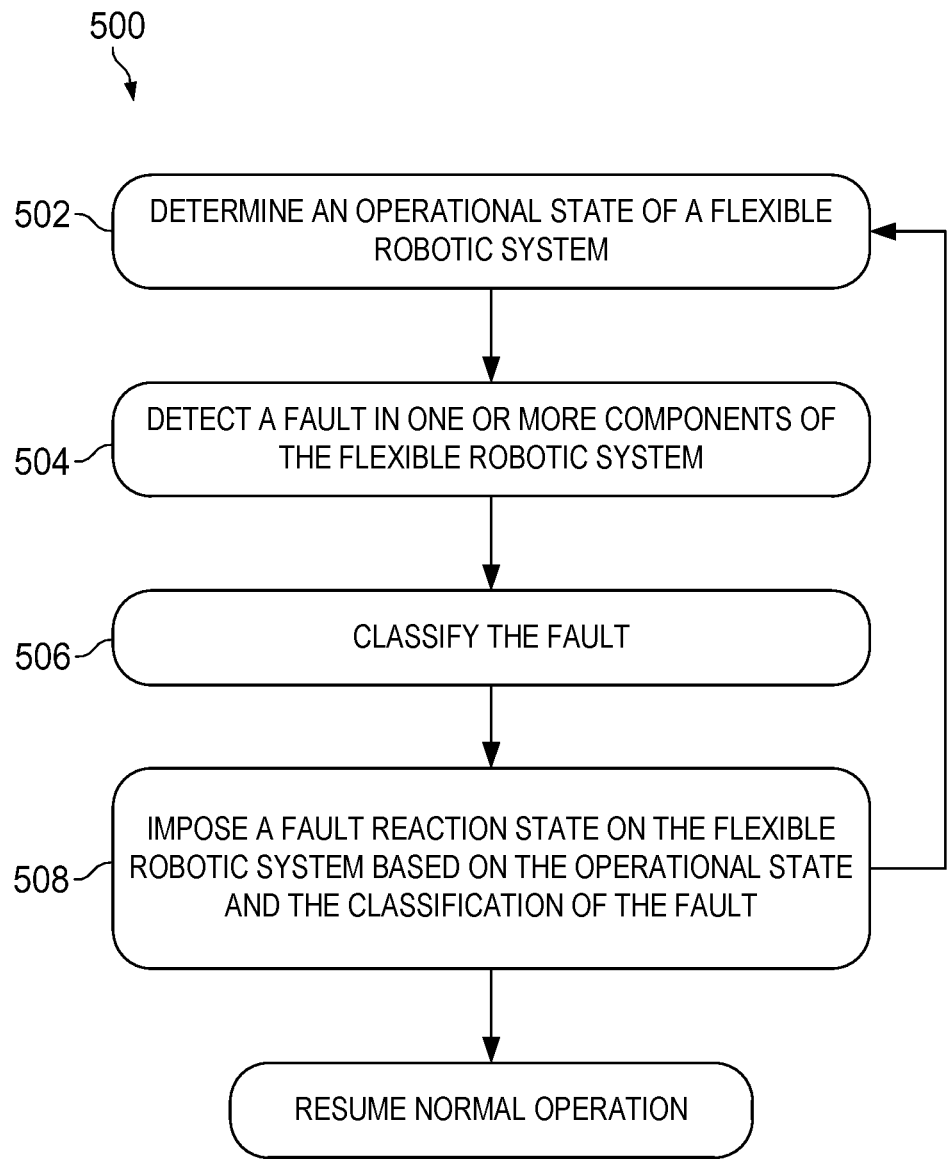

FIG. 5 is a flowchart illustrating a method for mitigating faults in a medical robotic system according to some embodiments of the present disclosure.

Figure 6A:
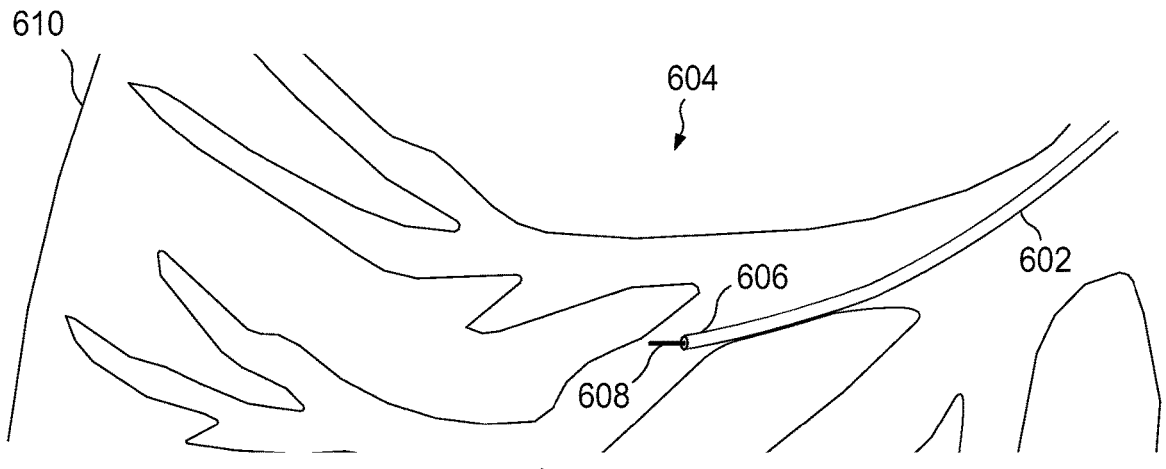
Figure 6B:
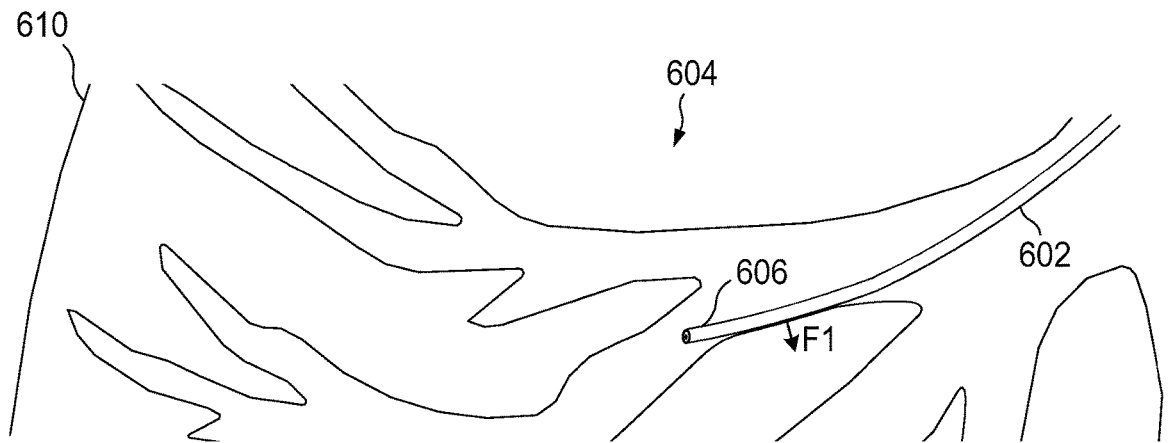
Figure 6C:
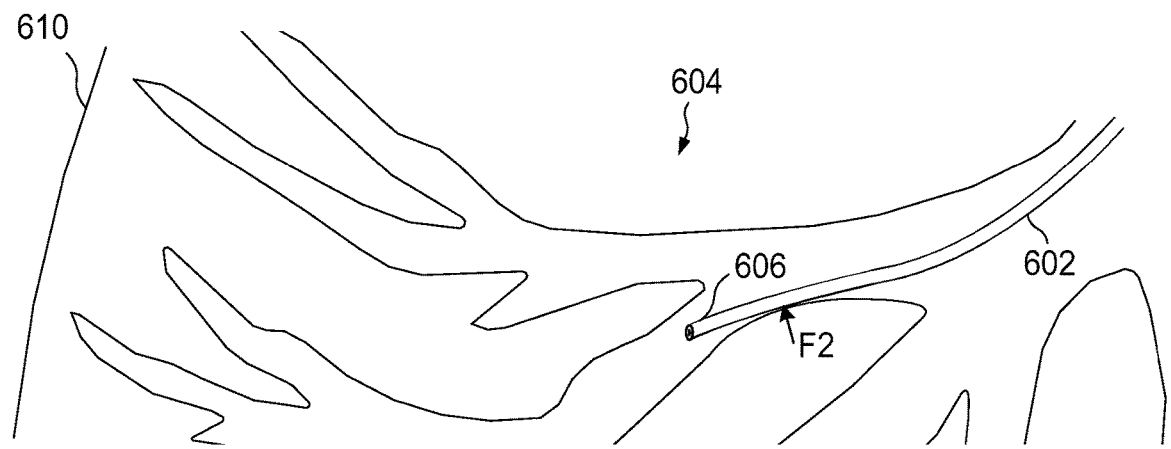

FIGS. 6A, 6B, and 6C illustrate stages responsive to a fault detected in a medical robotic system positioned within a human lung according to aspects of the present disclosure.

Figure 7:
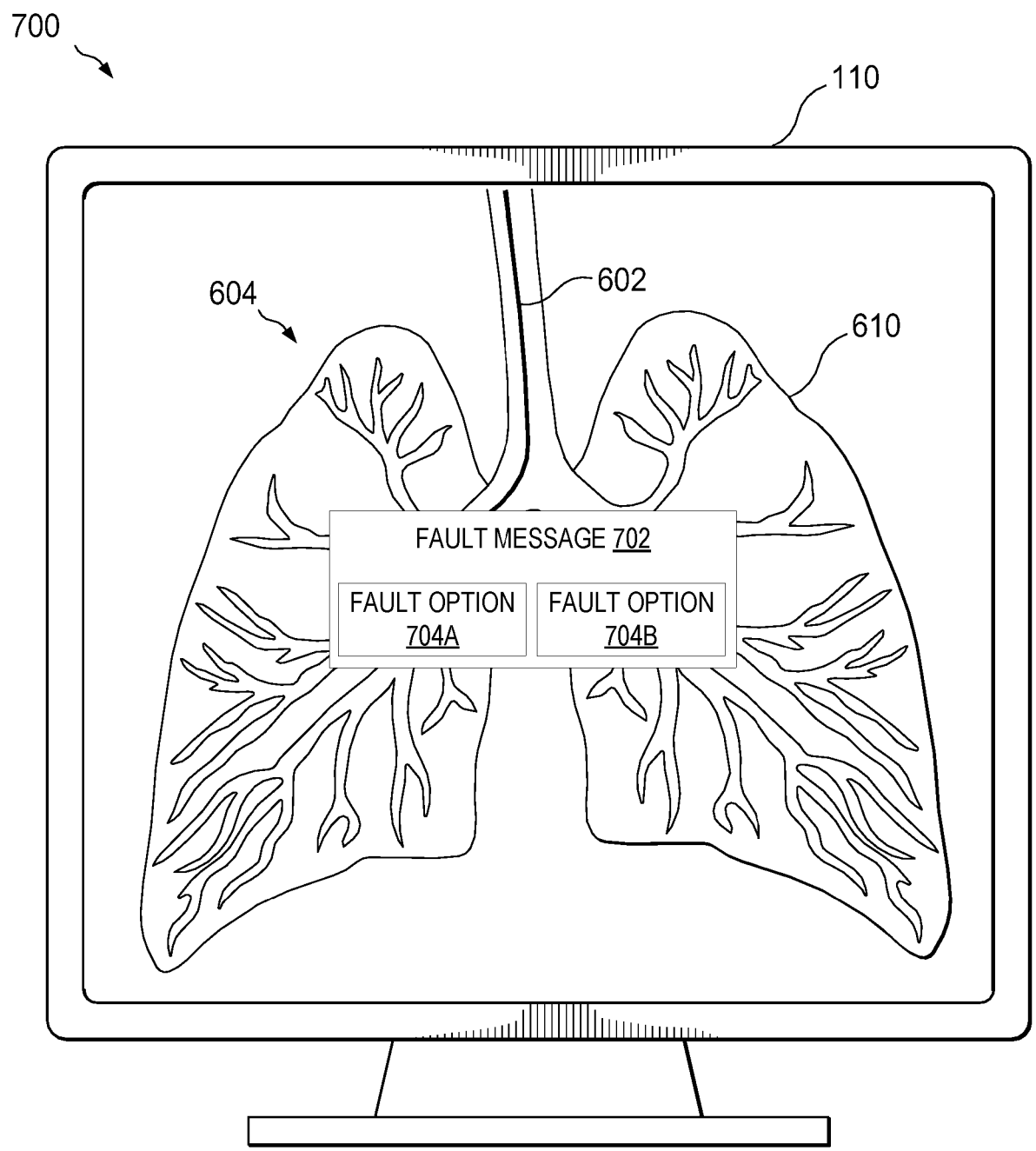

FIG. 7 illustrates a graphical user interface that may be employed in some embodiments of the present disclosure.

These drawings may be better understood by reference to the following detailed description.

DETAILED DESCRIPTION

In the following detailed description of the aspects of the invention, numerous specific details are set forth in order to provide a thorough understanding of the disclosed embodiments. However, it will be obvious to one skilled in the art that the embodiments of this disclosure may be practiced without these specific details. In other instances well known methods, procedures, components, and circuits have not been described in detail so as not to unnecessarily obscure aspects of the embodiments of the invention. And, to avoid needless descriptive repetition, one or more components or actions described in accordance with one illustrative embodiment can be used or omitted as applicable from other illustrative embodiments.

The embodiments below will describe various instruments and portions of instruments in terms of their state in three-dimensional space. As used herein, the term "position" refers to the location of an object or a portion of an object in a three-dimensional space (e.g., three degrees of translational freedom along Cartesian x-, y-, and z-coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

Figure 1:
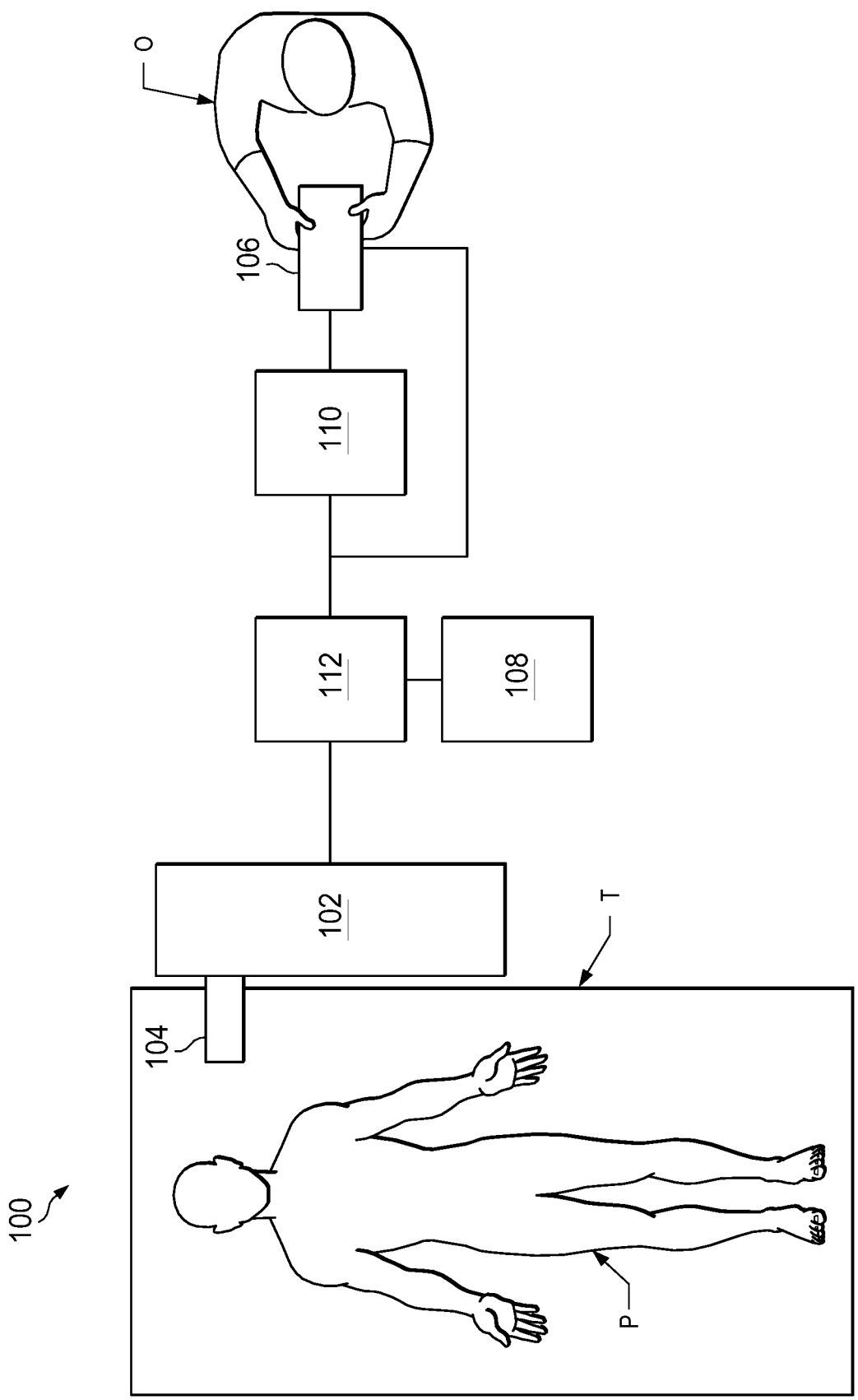
FIG. 1 is a teleoperated medical system, in accordance with embodiments of the present disclosure.

Referring to FIG. 1 of the drawings, a teleoperational medical system 100 for use in, for example, surgical, diagnostic, therapeutic, or biopsy procedures, is generally indicated by the reference numeral 100. As shown in FIG. 1, the teleoperational medical system 100 generally includes a teleoperational manipulator assembly 102 (also called "slave manipulator assembly 102", teleoperational assembly 102, and manipulator assembly 102) that has one or more instrument systems, such as the medical instrument system 104 in performing various procedures on the patient P. The manipulator assembly 102 is mounted to or near an operating table T. An operator input system called a master assembly 106 allows an operator (e.g., a surgeon, a clinician, or the physician O as illustrated in FIG. 1) to view the interventional site and to control the manipulator assembly 102.

The master assembly 106 may be located at an operator's console which is usually located in the same room as operating table T and may be positioned proximate the operating table T. However, it should be understood that the physician O can be located in a different room or a completely different building from the patient P. Master assembly 106 generally includes one or more control devices for controlling the manipulator assemblies 102. The control devices may include any number of a variety of input devices, such as joysticks, trackballs, data gloves, trigger-guns, hand-operated controllers, voice recognition devices, body motion or presence sensors, or the like. In some embodiments, the control devices will be provided with the same degrees of freedom as the one or more associated medical instrument system(s) 104 to provide the physician with telepresence, or the perception that the control devices are integral with the instrument system 104 so that the physician has a strong sense of directly controlling the instrument system 104. In other embodiments, the control devices may have more or fewer degrees of freedom than the associated medical instrument system 104 and still provide the physician with telepresence. In some embodiments, the control devices are manual input devices which move with six degrees of freedom, and which may also include an actuatable handle for actuating instruments (for example, for closing grasping jaws, applying an electrical potential to an electrode, delivering a medicinal treatment, or the like).

The a portion of the manipulator assembly 102 supports the medical instrument system 104 and may include a kinematic structure of one or more non-servo controlled links (e.g., one or more links that may be manually positioned and locked in place, generally referred to as a set-up structure) and a teleoperational manipulator. The manipulator assembly 102 includes plurality of actuators or motors that drive inputs on the medical instrument system 104 in response to commands from the control system (e.g., a control system 112). The motors include drive systems that when coupled to the medical instrument system 104 may advance the medical instrument into a naturally or surgically created anatomic orifice. Other motorized drive systems may move the distal end of the medical instrument in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the motors can be used to actuate an articulable end effector of the instrument for grasping tissue in the jaws of a biopsy device or the like. Motor position sensors such as resolvers, encoders, potentiometers, and other mechanisms may provide sensor data to the teleoperational assembly describing the rotation and orientation of the motor shafts. This position sensor data may be used to determine motion of the objects manipulated by the motors.

The teleoperational medical system 100 also includes a sensor system 108 with one or more sub-systems for receiving information about the instruments and instrument systems of the manipulator assembly 102. Such sub-systems may include a position/location sensor system (e.g., an electromagnetic (EM) sensor system); a shape sensor system for determining the position, orientation, speed, velocity, pose, and/or shape of the catheter tip and/or of one or more segments along a flexible body of the instrument system 104; and/or a visualization system for capturing images from the distal end of the catheter system.

The visualization system (e.g., visualization system 231 of FIG. 2) may include a viewing scope assembly that records a concurrent or real-time image of the surgical site at the distal end of the medical instrument system 104 and provides the image to the physician O in one or more visual displays. The concurrent image may be, for example, a two- or three-dimensional image captured by an endoscope positioned within the surgical site. In this embodiment, the visualization system includes endoscopic components that may be integrally or removably coupled to the medical instrument system 104. However in alternative embodiments, a separate endoscope, attached to a separate manipulator assembly may be used with the medical instrument to image the surgical site. The visualization system 231 may be implemented as hardware, firmware, software or a combination thereof which interact with or are otherwise executed by one or more computer processors, which may include the processors of a control system 112 (described below). The processors of the control system 112 may execute instructions comprising instructions corresponding to processes disclosed herein, such as these visualization processes and others.

The teleoperational medical system 100 also includes a display 110 for displaying an image or representation of the surgical site and medical instrument system 104 generated by sub-systems of the sensor system 108. The display 110 and the master assembly 106 may be oriented so the physician can control the medical instrument system 104 and the master assembly 106 with the perception of telepresence. In some embodiments, the display 110 may present a model of one or more objects to be displayed to the physician O. For example, a model of an organ or anatomic structure passageway of the patient P (or a model that is not specific to the patient P) may be displayed. As another example, a model of the medical instrument system 104 or a component thereof may be displayed as well.

The display 110 may also display an image of the surgical site and medical instruments captured by the visualization system 231. The display 110 and the control devices may be oriented such that the relative positions of the imaging device in the scope assembly and the medical instruments are similar to the relative positions of the physician's eyes and hands so the physician can manipulate the medical instrument system 104 and the hand control as if viewing the workspace in substantially true presence. By true presence, it is meant that the presentation of an image is a true perspective image simulating the viewpoint of an operator that is physically manipulating the instrument system 104.

Alternatively or additionally, the display 110 may present images of the surgical site recorded pre-operatively or intra-operatively using image data from imaging technology such as, computed tomography (CT), magnetic resonance imaging (MRI), fluoroscopy, thermography, ultrasound, optical coherence tomography (OCT), thermal imaging, impedance imaging, laser imaging, or nanotube X-ray imaging. The pre-operative or intra-operative image data may be presented as two-dimensional, three-dimensional, or four-dimensional (including e.g., time based or velocity based information) images or as images from models created from the pre-operative or intra-operative image data sets.

In some embodiments, often for purposes of image-guided medical procedures, the display 110 may display a virtual navigational image in which the actual location of the medical instrument system 104 is registered (i.e., dynamically referenced) with the preoperative or concurrent images/model to present the physician O with a virtual image of the internal surgical site from the viewpoint of the location of the tip of the instrument system 104. An image of the tip of the instrument system 104 or other graphical or alphanumeric indicators may be superimposed on the virtual image to assist the physician controlling the medical instrument. Alternatively, the instrument system 104 may not be visible in the virtual image.

In other embodiments, the display 110 may display a virtual navigational image in which the actual location of the medical instrument is registered with preoperative or concurrent images to present the physician O with a virtual image of a medical instrument within the surgical site from an external viewpoint. An image of a portion of the medical instrument or other graphical or alphanumeric indicators may be superimposed on the virtual image to assist the physician controlling the instrument system 104. In some embodiments, a virtual navigational image may be presented in the display 110 that depicts a model of an anatomical passageway from a perspective of an instrument being inserted along or through a corresponding actual anatomical passageway.

The teleoperational medical system 100 also includes a control system 112. The control system 112 includes at least one memory and at least one computer processor (not shown), and typically a plurality of processors, for effecting control between the medical instrument system 104, the master assembly 106, the sensor system 108, and the display 110. The control system 112 also includes programmed instructions (e.g., a computer-readable medium storing the instructions) to implement some or all of the methods described in accordance with aspects disclosed herein, including instructions for providing pathological and/or physiological information to the display 110. While control system 112 is shown as a single block in the simplified schematic of FIG. 1, the system may include two or more data processing circuits with one portion of the processing optionally being performed on or adjacent the manipulator assembly 102, another portion of the processing being performed at the master assembly 106, and the like. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 112 supports wireless communication protocols such as Bluetooth, IrDA, HomeRF, IEEE 802.11, DECT, and Wireless Telemetry.

In some embodiments, control system 112 may include one or more servo controllers that receive force and/or torque feedback from the medical instrument system 104. Responsive to the feedback, the servo controllers transmit signals to the master assembly 106. The servo controller(s) may also transmit signals instructing the manipulator assembly 102 to move the medical instrument system 104 which extend into an internal surgical site within the patient's body via openings in the body. Any suitable conventional or specialized servo controller may be used. A servo controller may be separate from, or integrated with, manipulator assembly 102. In some embodiments, the servo controller and teleoperational assembly are provided as part of a teleoperational arm cart positioned adjacent to the patient's body.

The control system 112 may further include a virtual visualization system (like the visualization system 231 of FIG. 2) to provide navigation assistance to the medical instrument system 104 when used in an image-guided surgical procedure. Virtual navigation using the virtual visualization system is based upon reference to the acquired preoperative or intraoperative datasets and models of the anatomic passageways. More specifically, the virtual visualization system processes images of the surgical site imaged using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, or the like. Software alone or in combination with manual input is used to convert the recorded images into segmented two dimensional or three dimensional composite representation of a partial or an entire anatomic organ or anatomic region. An image data set is associated with the composite representation. The composite representation and the image data set describe the various locations and shapes of the passageways and their connectivity. The images used to generate the composite representation may be recorded preoperatively or intraoperatively during a clinical procedure. In an alternative embodiment, a virtual visualization system may use standard representations (i.e., not patient specific) or hybrids of a standard representation and patient specific data. The composite representation and any virtual images generated by the composite representation may represent the static posture of a deformable anatomic region during one or more phases of motion (e.g., during an inspiration/expiration cycle of a lung).

During a virtual navigation procedure, the sensor system 108 may be used to compute an approximate location of the instrument or locations of portions of the instrument with respect to the patient anatomy. The location(s) can be used to produce both macro-level (external) tracking images of the patient anatomy and virtual internal images of the patient anatomy. Various systems for using electromagnetic (EM) sensors, fiber optic sensors, or other sensors to register and display a medical implement together with preoperatively recorded surgical images, such as those from a virtual visualization system, are known. For example U.S. patent application Ser. No. 13/107,562 (filed May 13, 2011) (disclosing "Medical System Providing Dynamic Registration of a Model of an Anatomic Structure for Image-Guided Surgery") which is incorporated by reference herein in its entirety, discloses one such system.

The control system 112 may also be configured to detect and respond to system failures or faults or fault conditions. For example, motors or actuators used to control the medical instrument system 104 may include torque sensors or position sensors to facilitate control by the control system 112. The medical instrument system 104 may include motors or actuators having redundant sensors to monitor those motors or actuators. When redundant sensors provide different readings (e.g., readings that differ by more than a threshold amount), the control system 112 may detect that this difference is a fault in the medical system 100. In some examples faults are not necessarily indicative of a failure or error but a status or condition change can be detected with other changes in system conditions. As is discussed in more detail further below, the control system 112 may adjust or change operational states of the medical system 100 or individual components thereof to mitigate potentially adverse consequences.

The teleoperational medical system 100 may further include optional operation and support systems (not shown) such as illumination systems, steering control systems, irrigation systems, and/or suction systems. In alternative embodiments, the teleoperational system may include more than one teleoperational assembly and/or more than one operator input system. The exact number of manipulator assemblies will depend on the surgical procedure and the space constraints within the operating room, among other factors. The physician input systems may be collocated or they may be positioned in separate locations. Multiple operator input systems allow more than one operator to control one or more manipulator assemblies in various combinations.

FIG. 2 illustrates a flexible robotic system, referred to in this context as a medical instrument system 200, which may be used as the medical instrument system 104 in an image-guided medical procedure performed with teleoperational medical system 100. Alternatively, the medical instrument system 200 may be used for non-teleoperational exploratory procedures or in procedures involving traditional manually-operated medical instruments, such as endoscopy. Additionally or alternatively, the medical instrument system 200 may be used to gather (i.e., measure) a set of data points corresponding to locations within patient anatomic passageways.

The instrument system 200 includes a catheter system 202 coupled to a housing 204, also referred to as a backend housing. In embodiments in which the instrument system 200 is manually operated, the housing 204 may include gripping features, manual actuators, or other components for manually controlling the motion of the instrument system. The catheter system 202 may be steerable or, alternatively, the system may be non-steerable without an integrated mechanism for operator control of the instrument bending. The catheter system 202 includes an elongate flexible body 216 having a proximal end 217 and a tip portion or distal end 218. In one embodiment, the elongate flexible body 216 has an approximately 3 mm outer diameter. Other flexible body outer diameters may be larger or smaller. The catheter system 202 may optionally include a shape sensor 222 for determining the position, orientation, speed, velocity, pose, and/or shape of the catheter tip at distal end 218 and/or of one or more segments 224 along the flexible body 216. The entire length of the flexible body 216, between the distal end 218 and the proximal end 217, may be effectively divided into the segments 224. If the instrument system 200 is a medical instrument system 104 of a teleoperational medical system 100, the shape sensor 222 may be a component of the sensor system 108. If the instrument system 200 is manually operated or otherwise used for non-teleoperational procedures, the shape sensor 222 may be coupled to a tracking system 230 that interrogates the shape sensor and processes the received shape data.

The shape sensor 222 may include an optical fiber aligned with the flexible body 216 (e.g., provided within an interior channel (not shown) or mounted externally). In one embodiment, the optical fiber has a diameter of approximately 200 μm. In other embodiments, the dimensions may be larger or smaller. The optical fiber of the shape sensor 222 forms a fiber optic bend sensor for determining the shape of the catheter system 202. In one alternative, optical fibers including Fiber Bragg Gratings (FBGs) are used to provide strain measurements in structures in one or more dimensions. The optical fiber of the shape sensor 222 may enable the simultaneous collection of a set of measured points that describe the positions of various portions of the shape sensor 222 along the length of the flexible body 216 at a single moment in time. In some embodiments, the shape sensor 222 may include an optical fiber having more than one optical fiber core or multiple optical fibers having more than one core. For example, the shape sensor 222 may include an optical fiber having seven optical fiber cores, which may be individually interrogated to provide redundancy and to provide increased accuracy. Various systems and methods for monitoring the shape and relative position of an optical fiber in three dimensions are described in U.S. Provisional Patent Application No. 62/334,649 (filed May 11, 2016) (entitled "Redundant Core In Shape Fiber for Safety"); U.S. patent application Ser. No. 11/180,389 (filed Jul. 13, 2005) (entitled "Fiber optic position and shape sensing device and method relating thereto"); U.S. patent application Ser. No. 12/047,056 (filed on Jul. 16, 2004) (entitled "Fiber-optic position and/or shape sensing based on Rayleigh scatter"); and U.S. Pat. No. 6,389,187 (filed on Jun. 17, 1998) (entitled "Optical Fibre Bend Sensor"), which are all incorporated by reference herein in their entireties.

Sensors in alternative embodiments may employ other suitable strain sensing techniques, such as Rayleigh scattering, Raman scattering, Brillouin scattering, and fluorescence scattering. In other alternative embodiments, the shape of the catheter may be determined using other techniques. For example, the history of the catheter's distal tip pose can be used to reconstruct the shape of the device over the interval of time. As another example, historical pose, position, or orientation data may be stored for a known point of an instrument system along a cycle of alternating motion, such as breathing. This stored data may be used to develop shape information about the catheter. Alternatively, a series of positional sensors, such as electromagnetic (EM) sensors, positioned along the catheter can be used for shape sensing. Alternatively, a history of data from a positional sensor, such as an EM sensor, on the instrument system during a procedure may be used to represent the shape of the instrument, particularly if an anatomic passageway is generally static. Alternatively, a wireless device with position or orientation controlled by an external magnetic field may be used for shape sensing. The history of the wireless device's position may be used to determine a shape for the navigated passageways.

The medical instrument system may, optionally, include a position sensor system 220. The position sensor system 220 may comprise, or be a component of, an EM sensor system with one or more sensors including one or more conductive coils that may be subjected to an externally generated electromagnetic field. Further description of an EM sensor system is provided in U.S. Pat. No. 6,380,732 (filed Aug. 11, 1999) (disclosing "Six-Degree of Freedom Tracking System Having a Passive Transponder on the Object Being Tracked"), which is incorporated by reference herein in its entirety. In some embodiments, the shape sensor 222 may also function as the position sensor because the shape of the shape sensor 222 together with information about the location of the base of the shape sensor 222 (in the fixed coordinate system of the patient, referred to as "patient space") allows the location of various points along the shape sensor, including the distal tip, to be calculated.

The tracking system 230 may include the position sensor system 220 and/or a shape sensor 222 for determining the position, orientation, speed, pose, and/or shape of the distal end 218 and of one or more segments 224 along the instrument system 200. The tracking system 230 may be implemented as hardware, firmware, software or a combination thereof which interact with or are otherwise executed by one or more computer processors, which may include the processors of a control system 112. The tracking system 230 may include one or more sensors that monitor the insertion of instruments, such as the medical instrument 226, through the lumen's extending along the length of the flexible body 216. Accordingly, the tracking system 230 may be relied upon to provide an indication of whether a distal tip of a medical instrument 226 is contained within its corresponding lumen or whether the distal tip is protruding out there from for use in a surgical procedure. For example, the medical instrument 226 may include a needle in some embodiments. The tracking system 230 may provide information to the control system 112 to indicate an insertion depth of the needle and movement along an insertion axis, including whether or not the needle is positioned beyond the distal end 218 for use in a biopsy procedure, for example. In some embodiments, the housing 204 may include a medical instrument detector to indicate whether a medical instrument or other inner instrument body has been inserted through a lumen in the flexible body 216 and to measure insertion/retraction distances.

The flexible body 216 includes a channel sized and shaped to receive a medical instrument 226. Medical instruments may include, for example, image capture probes, biopsy instruments, laser ablation fibers, or other surgical, diagnostic, or therapeutic tools. Medical tools may include end effectors having a single working member such as a scalpel, a blunt blade, an optical fiber, a needle, or an electrode. Other end effectors may include, for example, forceps, graspers, scissors, or clip appliers. Examples of electrically activated end effectors include electrosurgical electrodes, transducers, sensors, and the like. In various embodiments, the medical instrument 226 may be an image capture probe that includes a distal portion with a stereoscopic or monoscopic camera at or near the distal end 218 of the flexible body 216 for capturing images (including video images) that are processed by a visualization system 231 for display. The image capture probe may include a cable coupled to the camera for transmitting the captured image data. Alternatively, the image capture instrument may be a fiber-optic bundle, such as a fiberscope, that couples to the visualization system. The image capture instrument may be single or multi-spectral, for example capturing image data in one or more of the visible, infrared, or ultraviolet spectrums.

The medical instrument 226 may house cables, linkages, or other actuation controls (not shown) that extend between the proximal and distal ends of the instrument to controllably bend, position, and/or otherwise manipulate the distal end of the instrument. Steerable instruments are described in detail in U.S. Pat. No. 7,316,681 (filed on Oct. 4, 2005) (disclosing "Articulated Surgical Instrument for Performing Minimally Invasive Surgery with Enhanced Dexterity and Sensitivity") and U.S. patent application Ser. No. 12/286,644 (filed Sep. 30, 2008) (disclosing "Passive Preload and Capstan Drive for Surgical Instruments"), which are incorporated by reference herein in their entireties.

The flexible body 216 may also houses cables, linkages, or other steering controls (not shown) that extend between the housing 204 and the distal end 218 to controllably bend the distal end 218 as shown, for example, by the broken dashed line depictions 219 of the distal end. Steerable catheters are described in detail in U.S. patent application Ser. No. 13/274,208 (filed Oct. 14, 2011) (disclosing "Catheter with Removable Vision Probe"), which is incorporated by reference herein in its entirety. In embodiments in which the instrument system 200 is actuated by a teleoperational assembly, the housing 204 may include drive inputs that removably couple to and receive power from motorized drive elements of the teleoperational assembly, such as the actuator 206.

In the illustrated embodiment, the actuator 206 is a rotational actuator that is coupled to the distal end 218 by a wire or cable 208. As the actuator 206 rotates around its axis, the length of the cable 208 changes, causing movement shown by the broken dashed line depictions 219. A first sensor 210A may be coupled to the actuator 206 to detect a position of the actuator 206, a direction of rotation, a rate of rotation, a state of the actuator, etc. The first sensor 210A may encode this information for use by the control system 112 of FIG. 1. Additionally, embodiments of the medical instrument system 200 may include a second sensor 210B that is also in communication with the actuator 206 to provide the same kind of information provided by the first sensor 210A. In some embodiments, the first and second sensors 210A-B may provide related information that is obtained through different sensing mechanism. For example, sensor 210A may measure the rotation of the actuator 206, while the sensor 210B measures translational motion of a wire or cable that corresponds to the rotation of the actuator 206. These related types of information may be used as redundant information. Accordingly, the first and second sensors 210A-B may be redundant sensors providing redundant information to the control system 112. Embodiments of the housing 204 may include three or more actuators like the actuator 206, with corresponding sensors. Additionally, some embodiments of the housing 204 are configured to interface with externally disposed actuators. For example, one or more actuators like actuator 206 may be disposed in a separate motor housing that couples to the housing 204 to drive corresponding shafts or capstans disposed within the housing 204. By driving the shafts or capstans, the wire or cable 208 may be wound or unwound to move the distal end 218 in a desired motion or to a desired position. In such embodiments, the first and second sensors 210A-B may be included in the separate motor housing.

In various embodiments, the medical instrument system 200 may include a flexible bronchial instrument, such as a bronchoscope or bronchial catheter, for use in examination, diagnosis, biopsy, or treatment of a lung. The system 200 may also be suited for navigation and treatment of other tissues, via natural or surgically created connected passageways, in any of a variety of anatomic systems, including the colon, the intestines, the kidneys and kidney calices, the brain, the heart, the circulatory system including vasculature, and the like. Embodiments further include non-medical applications, such as those for assembly line application or other industrial applications.

The information from the tracking system 230 may be sent to a navigation system 232 where it is combined with information from the visualization system 231 and/or the preoperatively obtained models to provide the physician with real-time position information on the display 110 for use in the control of the instrument system 200. The control system 112 may utilize the position information as feedback for positioning the instrument system 200. Various systems for using fiber optic sensors to register and display a surgical instrument with surgical images are provided in U.S. patent application Ser. No. 13/107,562, filed May 13, 2011, disclosing, "Medical System Providing Dynamic Registration of a Model of an Anatomic Structure for Image-Guided Surgery," which is incorporated by reference herein in its entirety.

As shown in in FIG. 2, medical instruments like the medical instrument 226 can be provided for such procedures as surgery, biopsy, ablation, illumination, irrigation, or suction and can be deployed through one or more channels extending through the flexible body 216 for use at a target location within the anatomy. If, for example, the instrument 226 is a biopsy instrument, it may be used to remove sample tissue or a sampling of cells from a target anatomic location. The medical instrument 226 may be used with an image capture probe also within the flexible body 216. Alternatively, the instrument 226 may itself be the image capture probe. The instrument 226 may be advanced from the opening of a correspondent lumen at the distal end 218 to perform the procedure and then retracted back into the lumen when the procedure is complete. The medical instrument 226 may be removed from the proximal end 217 of the catheter flexible body or from another optional instrument port (not shown) along the flexible body.

FIG. 2 also depicts a plurality of lumen openings 236 is included in the distal end 218 of the flexible body 216. These openings 236 may permit the physician O to utilize one or more medical instruments, such as the medical instrument 226, at a surgical site after positioning the distal end 218 at that site. The openings 236 may include openings specifically sized and shapes to receive specific instruments. For example, one lumen opening may provide access to an imaging instrument to permit visualization at the distal end 218. Another lumen opening may provide an opening for an ablation probe to be passed to gain access to the surgical site. Accordingly, each lumen opening 236 may correspond to a channel extending along a length of the elongate flexible body 216. This may facilitate the performance of medical procedures, including surgical procedures, in a minimally invasive manner.

The medical instrument system 200 further includes a fault monitor 240, which may be provided by software, hardware, or a combination thereof to monitor for faults or failures in the medical system 100. As described further herein, the fault monitor 240 may provide a fault reaction logic supervisor that classifies faults. For example faults may be classified as critical or noncritical. The fault monitor 240 may operate to direct the medical system 100 and/or components thereof like the medical instrument system 200 to respond to the faults depending on their classification and/or other identifying characteristics of the faults. For example, the fault monitor 240 may receive information from the first and second sensors 210A-B and identify a difference between the information provided by each sensor. The fault monitor 240 may determine whether that difference qualifies as a system fault and/or a level or classification of such a fault. In some embodiments, the fault monitor 240 may be included as a sub-system or service of the control system 112 of FIG. 1.

FIGS. 3A and 3B illustrate an exemplary surgical environment 300 according to some embodiments, in which a patient P is positioned on an operating table T. The patient P may be stationary within the surgical environment in the sense that gross patient movement is limited by sedation, restraint, or other means. Within the surgical environment 300, a medical instrument 304 is coupled to an instrument carriage 306. In various embodiments, the medical instrument 304 may use EM sensors, shape-sensors, and/or other sensor modalities. The instrument carriage 306 is mounted to an insertion stage 308 fixed within the surgical environment 300. Alternatively, the insertion stage 308 may be movable but have a known location (e.g., via a tracking sensor or other tracking device) within the surgical or patient coordinate system. The instrument carriage 306 may be a component of a teleoperational manipulator assembly (e.g., manipulator assembly 102) that couples the instrument 304 to control insertion motion and, optionally, motion of a distal end of the instrument in multiple directions including yaw, pitch, and roll. The instrument carriage 306 or the insertion stage 308 may include servomotors (not shown) that control motion of the instrument carriage along the insertion stage. Some embodiments of the instrument carriage 306 may include a drive motor housing that is separate from an instrument backend housing, as described above in connection with FIG. 2. In some embodiments, the medical instrument 304 may be provided by the medical instrument system 200 of FIG. 2. These servomotors or actuators may have one or more sensors to provide associated measurements to a control system, like the control system 112 of FIG. 1.

The medical instrument 304 may include a flexible catheter 310 coupled at a proximal end thereof to a rigid instrument housing 312. The rigid instrument housing 312 is coupled and fixed relative to the instrument carriage 306 The medical instrument 304 may be substantially similar to the medical instrument system 200, such that the catheter 310 corresponds to the flexible body 216 of FIG. 2.

A position measuring device 320 provides information about the position of the rigid instrument housing 312 as it moves on the insertion stage 308 along an insertion axis A. The position measuring device 320 may include resolvers, encoders, potentiometers, and other mechanisms that determine the rotation and orientation of the motor shafts controlling the motion of the instrument carriage 306 and consequently the motion of the rigidly attached instrument housing 312. Redundant information collection devices may provide redundant information regarding the position, velocity, etc. of the instrument carriage 306. In this embodiment, the insertion stage 308 is linear, but in alternative embodiments it may be curved or have a combination of curved and linear sections. FIG. 3A shows the instrument housing 312 and carriage 306 in a retracted position along the insertion stage 308. In FIG. 3B, the instrument housing 312 and the carriage 306 have advanced along the linear track of the insertion stage 308 and the distal end of the catheter 310 has advanced into the patient P. In this advanced position, the proximal point 316 is at a position $L_1$ on the axis A.

Embodiments of the medical instrument 304 may collect measured points using any number of modalities, including EM sensing and fiber optic shape-sensing. The set of measured points may be used to register a shape of the medical instrument 304 to a computer model of patient anatomy. For example, preoperative or intraoperative images may be collected of patient P and used to produce a three-dimensional computer model of a portion of anatomy. To enable the physician O to better view the surgical site and surrounding tissues, the model may be registered to the medical instrument 304 to bring them into a common space.

FIGS. 4A, 4B, 4C, and 4D illustrate the advancement of the catheter 310 of FIGS. 3A and 3B through anatomic passageways 402 of the lungs 400 of the patient P of FIGS. 1 and 3. These passageways 402 include the trachea and the bronchial tubes. As the catheter 310 is advanced as the carriage 306 moves along the insertion stage 308, the physician O may steer the distal end 318 of the catheter 310 to navigate through the anatomic passageways 402. In navigating through the anatomic passageways 402, the catheter 310 assumes a shape that may be measured by the shape sensor 314 extending within the catheter 310.

FIG. 5 is a flowchart illustrating a method 500 for controlling a flexible robotic system like the medical instrument system 200 of FIG. 2 and the instrument 304 of FIGS. 3A and 3B to detect, classify, and mitigate faults that may occur in the system. The method 500 is depicted as several enumerated steps or operations. Embodiments of these operations may provide a system for appropriate handling of faults given a particular state of the flexible robotic system and the position of components of the flexible robotic system with respect to a patient. Embodiments of the method 500 may include additional operations before, after, in between, or as part of the enumerated operations. Some embodiments of the method 500 may be implemented by a control system, such as the control system 112 of FIG. 1.

An embodiment of the method 500 may begin at operation 502 in which the control system 112 determines an operational state of the flexible robotic system. The operational state of the robotic system may include information characterizing a current configuration of the components of the flexible robotic system, such as an elongate flexible body thereof, like the flexible body 216 or the catheter 310. For example, the operational state may include information that positions the elongate flexible body within specific anatomical passageways of an organ, such as a lung. As shown in FIG. 6A, an elongate flexible body 602 is positioned within the passageways of a lung 604. The elongate flexible body 602 may include one or more optical fiber cores to provide shape information characterizing the flexible body 602. A registration between a model of the lung 604 and the shape of the flexible body 602 may provide information relating the lung 604 and the flexible body 602 as part of the operational state of the flexible robotic system. Further, the operational state may include a position of a distal end 606 of the flexible body 602. The operational state may further include information regarding type of tools which are inserted in the elongate flexible body 602 such as for example a biopsy tool, a vision probe, or an ablation instrument. As shown, a needle 608 is deployed from the distal end 606 within the passageways of the lung 604. For example, the needle 608 may be a biopsy needle being used in a biopsy procedure. Information describing the needle, such as its gauge size and construction information may be included in the operational state. Additionally, a step within a workflow may be included within the operational state. For example, the operational state may include an indication that the current workflow is at an insertion puncture step in a biopsy workflow. An insertion sensor may be used to determine how far the needle 608 is protruding from the distal end 606 of the flexible body 602. The operational state of the flexible robotic system may also include a drive mode of the system. For example, the operational state of the system may indicate that the system is in a "drive" mode, in which the intent of the physician is to drive the instrument and the system is disposed to react to and produce directed movements. Or the operational state may indicate the system is in a "lock" mode, in which the intent of the physician is to have the system maintain the current shape of the instrument. The physician O may select one of these modes or another mode by manipulating a virtual or physical user interface control via the master assembly 106. Other information, such as a distance away from the pleura 610 or another feature of the lung 604 may be included in the operational state of the flexible robotic system.

At operation 504, the control system 112 may detect a fault in one or more components of the flexible robotic system. For example, the control system 112 may determine that redundant sensors on a motor or actuator, like the actuator 206 of FIG. 2, are in disagreement or differ by more than a threshold amount. Another fault may be triggered by the problem with the registration between the model of the lung 604 and the flexible body 602, such that the registration should not be relied upon, at that time, to obtain a biopsy with the needle 608. A quality indicator of the registration, such as an error value may be used to determine whether the registration can be relied upon. Another fault may arise when a command is input at the master assembly 106 but no corresponding movement of the flexible body 602 with a needle 608 is observed by the control system 112. Similarly, a fault may arise when movement of the flexible body 602 or the needle 608 is observed by the control system in the absence of any affirmative command being received from the master assembly 106. Yet another fault may arise when a difference is detected between a commanded movement and a shape or pose of the medical instrument, indicating that a movement that was not intended by the physician O has resulted. In one example, encoders for measurement of rotational actuators providing change in cable length such as sensors 210A or 210B, can be used to calculate an expected shape of the flexible body 602 in a similar manner as would be calculated for flexible body 216. A fault may arise when a difference between the calculated or expected shape and the measured shape, measured with shape sensors such as shape sensor 314, is detected. Additionally, faults may arise during the execution of code by any component of the teleoperational medical system 100, including the manipulator assembly 102, the master assembly 106, the sensor system 108, and the control system 112 itself. In general, a fault may be any indication of a potentially unsafe operational state. For example, the sensors 210A-B of FIG. 2 may provide different indications of the state of the actuator 206 being used to control the distal end 606 of the flexible body 602 of FIG. 6. The fault may indicate the unreliability of information coming from the sensors 210, and the operational state may indicate that the needle 608 is extending from the distal end 606 by about 3 mm. Another fault may arise the information coming from sensor 222 is determined by the control system 112 to be faulty data.

At operation 506, the control system classifies the fault in order to provide an appropriate response that will ensure the highest level of safety of the patient P. Many different heuristics may be used to classify detected faults. Such heuristics may include the system or subsystem implicated by the fault, such as a motion system, a physiological sensing system, a communication system. A fault may implicate both the originating system, i.e., the system in which the fault originated) as well as systems that are dependent on those originating system. For example, a secondary fault in a motion actuation system may be implicated by a primary fault in a sensor system used to provide pose information associated with a component to be moved. For example, a fault may be classified as a motion actuation fault when the fault indicates a failure regarding motion or position of the flexible elongate body, such as a disagreement between two redundant sensors or an error value associated with a current registration above a certain threshold. Motion actuation faults may indicate a current tracking error, a runaway control loop, or a faulty primary or secondary feedback sensor. For example, a disagreement between redundant sensors, such as sensors 210A-B, would be classified by the control system 112 as a motion actuation fault.

A motion actuation fault may be further classified based on the type of sensor detecting a failure. For example, a failure in a measurement sensor, such as a distal measurement sensor measuring a bending tip angle of a distal end of the flexible elongate body, may be classified as a distal sensor fault. The distal measurement sensor can include a fiber optic sensor, such as shape sensor 222, positioned from the distal end to a proximal end of the elongate flexible body, multiple EM sensors positioned near the distal end of the flexible elongate body, or a distal encoder to measure the bending tip angle of the distal end of the flexible elongate body. The distal measurement can also include proximal sensors at a proximal end of the flexible elongate body. The proximal sensors can include motor encoders on actuators configured to drive cables within the flexible elongate body, such as sensor 210A on actuator 206 driving cables 208 that cause catheter system 202 to bend. Rotation of actuators measured by the motor encoders combined with information of a medical instrument system such as medical instrument system 200 can be used to calculate an expected bending tip angle. Medical instrument system information can include measurements or estimations of friction in a drivetrain between input motors and output actuators, compliance in a flexible body, expected deformation of cables, and/or the like.

A detected fault can be classified as a distal sensor fault when there is a failure of the distal measurement sensor itself, for example when redundant fiber cores within the fiber optic sensor give readings that exceed a threshold difference. Alternatively, a fault can be classified as a distal sensor fault when the distal measurement sensor provides low quality readings including readings which exceed a specified noise threshold or readings that exhibit excessive variance above a threshold. In another example, a disagreement between redundant sensors, such as sensors 210A-B, exceeding a threshold would indicate an error in the proximal sensors. In another example, a disagreement between multiple distal measurement sensors such as the distal encoder and the motor encoders or between the fiber optic sensor and the motor encoders will be detected as a distal sensor fault.

Occurrence of errors can be used to further classify detected faults. For example, the distal measurement sensor may exhibit discrepancies outside of a threshold but may only be exhibiting the errors sporadically over a period of time. In one example, the fault may be detected and classified only if the errors are detected for a certain number of consecutive servo-cycles of a control loop. In some examples, data that has been classified as noisy can be combined with information from a combination of multiple distal measurement sensors to supplement the distal measurement sensor readings. For example, the noisy data can be supplemented with information through a filter (such as a Kalman filter), combining proximal sensor information, distal sensor information, and a model of the drivetrain to produce a more accurate and robust estimate of the bending tip angle which could be more tolerant to high noise level readings. A fault may alternatively be classified as a non-motion actuation fault when the fault indicates a failure that is not associated with motion or position of the flexible elongate body. Non-motion-actuation faults may be faults related to a display system or a communication system or faults related to algorithms and corresponding code associated with aspects other than the motion and pose of the elongate flexible member and/or instruments introduced thereby.

Another heuristic or factor that may be weighed may include a type of fault. For example, a fault associated with a physical component may be different than a fault associated with a bug in software that manifests during runtime.

At 508, the control system 112 imposes a fault reaction state on the flexible robotic system based on the operational state of the flexible robotic system and the classification of the fault detected by the control system 112. When the flexible robotic system is positioned within the anatomy of a patient P, the appropriate response to a fault may depend on several factors that can be obtained from the classification of the fault and the operational state. For example, an appropriate response to a motion actuation fault may be to lock the flexible body 602 in position such that forces acting upon it are actively resisted, i.e. actuators are activated to provide an opposing force in effort to maintain the pose of the elongate body. Another appropriate response to a motion actuation fault may be to control actuators (e.g. apply reduced torque, deactivate actuators, or transition a proportional part of the control signal to zero) coupled to the flexible body 602 to reduce an effective stiffness of the flexible body 602 or enable maximum compliance with any forces applied thereto by the surrounding anatomy. Yet another appropriate response to a motion actuation fault may be to activate the actuators sufficient to provide some resistance to forces on the flexible body 602 without activating the actuators with sufficient force to maintain the pose at the time the fault was detected.

Similarly, the fault reaction state may direct movement of one or more instruments positioned within or protruding from the distal end 606 of the flexible body 602. For example, upon detecting a fault, the control system 112 determines that the operational state indicates that the needle 608 is protruding out from the distal end 606 the elongate flexible body 602. A registration between the elongate flexible body 602 and a model of lung 604 may indicate that the elongate flexible body 602 is applying a force F1 to a portion of the lung 604. Rather than relax the pose of the elongate flexible body 602, the fault reaction state may direct withdrawal of the needle 608. In some embodiments, the control system 112 may communicate with the housing 204, which may include a motor or actuator system to insert and withdraw the needle 608 and the elongate flexible body 602, to cause automatic withdrawal of the needle 608. This withdrawal may be limited along the insertion axis of the medical instrument including the needle 608, such that the needle 608 remains proximate the distal end 606 but is wholly contained within the elongate flexible body 602. In this manner, the control system 112 may prevent the needle 608 from contacting the walls of the anatomical passageways of the lungs 604. In some embodiments, after the needle 608 is retracted back into the flexible body 602, the physician O or another operator may manually disengage the flexible body 602, such that it becomes compliant with forces imposed by the lung 604 or other anatomic structures. The control system 112 may detect the disengagement and reflect this as a change in the operational state of the flexible robotic system.

The withdrawal of the needle 608, or another medical instrument, back into the flexible body 602 may result in a change of the operational state of the flexible robotic system. The control system 112 may detect this change in the operational state and determine whether the current fault reaction state should be maintained, removed, or replaced by a different fault reaction state. For example, after the needle 608 is safely retracted, the control system 112 may de-energize actuators previously used to lock the elongate flexible body 602 in its pose at the time the fault was detected. The de-energized actuators may provide no resistance or decreased resistance to a restorative force F2 placed on the elongate flexible body 602 by the walls of the lung 604. As shown in FIG. 6C, the new fault reaction state may permit the elongate flexible body to comply with the force F2 (which is present in FIGS. 6A and 6B but counteracted by the force F1) changing the shape of the elongate flexible body 602 in response.

In some embodiments, the fault reaction state may include actions with respect to both the elongate flexible body 602 and the needle 608 that may be performed simultaneously or in conjunction. For example, the elongate flexible body 602 may be locked into position at the same time that the needle 608 is being retracted. In another example, the effective stiffness of the elongate flexible body 602 may be reduced at a specified rate over time while the needle 608 is simultaneously retracted. In an alternative example, the effective stiffness of the elongate flexible body 602 may be reduced at a specified rate over time while the elongate flexible body 602 is simultaneously retracted, which in turn retracts the needle 608. Thus, if the needle is inserted within tissue of the walls of the lung 406 during a fault, the elongate flexible body 602 may automatically retract the needle 608, withdrawing it from tissue while the elongate flexible body 602 is reduced in stiffness preventing potential damage to tissue by the needle. With either an automatic retraction of the needle 608 or an automatic retraction of the flexible elongate body 602, or both, the retraction can be over a specified retraction distance and once complete, insertion stage motors or insertion actuators controlling an insertion of the needle 608 or an insertion of the elongate flexible body 602, such as insertion stage 308 of FIGS. 3A and 3B, the control system may park or lock movement of needle 608 or elongate flexible body 602 along an insertion axis. The insertion actuators can be placed in an active servo control mode or the insertion actuators may be disabled and a brake may be engaged, locking the insertion position of the needle 608 and/or the elongate flexible body 602. The effective stiffness of the elongate flexible body 602 can be reduced accord to a profile providing decreased or no resistance to a restorative force F2 placed on the elongate flexible body 602 by the walls of the lung 604 at the time the retraction of the needle 608 or the elongate flexible body 602 has been completed.

In other embodiments, the control system 112 may first relax the elongate flexible body 602. The relaxed state of the elongate flexible body 602 may then be included in the operational state. The control system 112 may impose a new fault reaction state wherein the needle 608 is automatically retracted into the relaxed elongate flexible body 602. For example, if the operational state indicates that the distal end 606 of the elongate flexible body 602 or a distal end of the needle 608 is within a threshold distance from the pleura 610, the initial fault reaction state may retract the needle 608 before relaxing the elongate flexible body. In other words, the initial fault reaction state may include retracting the needle 608 and locking the elongate flexible body 602. When a change is detected in the operational state, a new fault reaction state may be directed by the control system 112. In some embodiments, the fault reaction state may include a sequence of operations that are performed either without reference to a change in the operational state or unless a counter-indicating operational state is detected. In other embodiments, the fault reaction state may include a single operation, which when performed results in a new operational state. And as indicated, if the fault is still present when the new operational state is reached, a new fault reaction state may be imposed by the control system, and the method may move from operation 508 to operation 502.

In general, the control system 112 may check for faults on a regular basis, such as a certain number of times a second. For example, the control system 112 may check for faults around 1000 times a second. The frequency of checks performed by the control system 112 helps prevent system failures that may compromise patient safety and may facilitate mitigation of such failures or faults by taking the appropriate actions with as little delay as possible. In some embodiments, a particular fault may need to be detected for multiple consecutive detection cycles or for a certain percentage of a plurality of detection cycles. For example, if a fault related to a localization sensor is detected and lasts for more than 20 ms (or another threshold time value such as 10 ms or 5 ms) the control system 112 may then take action to impose an appropriate fault reaction state on the flexible robotic system. Such threshold time periods may be set individually for specific faults and at specific steps in a surgical workflow. For example, the control system 112 may cause the cables to relax, permitting the flexible elongate body to enter a passive state in which it is compliant with forces applied by anatomical structures surrounding flexible elongate body. If the fault ends or is no longer detected by the time the time period ends, the control system 112 may take no action. In some embodiments, data collected from a related system during the time period of the fault may be discarded. Additionally, the control system 112 may "lock" the flexible robotic system for a period of time during which the fault may be addressed, such as by operator input or an operator action. In other embodiments, the control system 112 may indicate that a restart of the flexible robotic system may be required.

In some embodiments, errors or discrepancies may not result in a detected fault but may cause the control system to impose a fault reaction state. For example, patient movement or movement of a patient table T can cause registration to be incorrect. In another example, the physician O or medical personnel may clutch a manipulator assembly, such as manipulator assembly 102, and manually alter a position of a flexible elongate body, such as flexible body 602, within the patient P, potentially causing damage to the patient anatomy. The control system would impose a fault reaction state reducing an effective stiffness of the flexible body to avoid damage to the patient anatomy. In alternative embodiments, patient movement, movement of the patient table T, or manual movement of the manipulator assembly could be considered faults that are classified and result in the control system imposing a fault reaction state.

Referring now to FIG. 7, in some embodiments, the fault reaction state imposed by the control system 112 may include a notification or alert to an operator such as the physician O or another operator working beside the physician O. FIG. 7 depicts an embodiment of the display 110 of FIG. 1, showing a graphical user interface 700. The display 110 shows an image of the lungs 604 described above in connection with FIGS. 6A-C, along with an image of the elongate flexible body 602. The image of the lung 604 may be provided by a model derived from preoperative or intraoperative images. Similarly, the image of the elongate flexible body 602 may be derived from pose data obtained from one or more sensors distributed along the elongate flexible body 602, such as a shape sensing optical fiber extending the length thereof. After registration, the model of the lungs 604 and the model of the elongate flexible body 602 may be rendered jointly to facilitate navigation and operation within the confines of an internal surgical site that cannot be viewed externally. When a fault condition occurs, the control system 112 may cause a fault message 702 to be rendered to the display 110. The location of the fault message 702 may depend on the classification of the fault and the operational state of the flexible robotic system. For example, the control system 112 may cause a fault message 702 responsive to a motion actuation fault to be displayed so as to obstruct a view of the distal end 606 of the elongate flexible body 602. When the operative end of the elongate flexible body 602 is obstructed from view, the physician O may naturally cease issuing commands through the master assembly 106. In other embodiments, even when a motion actuation fault is detected, the control system 112 may cause the fault message 702 to appear in an area of the display 110 that does not obstruct the view of the distal end of the elongate flexible body 602.

In some embodiments, the fault message 702 may include instructions for the physician or another operator of the flexible robotic system. For example, the fault message 702 may indicate to the physician O that one or more medical instruments, such as the needle 608, should be manually removed from or manually retracted back into the elongate flexible body 602. As another example, the fault message 702 may indicate to the physician O that the needle 608 will automatically be retracted back into the elongate flexible body 602 such that no portion of the needle 608 protrudes out from the distal end 606 of the elongate flexible body 602. The fault message 702 may further include one or more fault options 704 (fault options 704A and 704B are depicted) that may be selectable user interface elements whereby the physician O or another operator may communicate to the control system 112 a desire for one fault reaction state over another given a set of conditions communicated to the physician O by the fault message 702. Additionally, the physician O may indicate to the control system 112 that a manual action indicated in the fault message 702 has been performed. For example, the fault message 702 may indicate a motion actuation fault has been detected and that the needle 608, or any other surgical instrument, should be removed from the elongate flexible body 602 or retracted therein. When the control system 112 is not able to automatically perform the withdrawal or retraction, the physician O may be instructed to do so and may select a fault option 704 to communicate to the control system 112 that this action has been manually performed, such that the control system 112 can resume further fault mitigation operations or can resume normal operation as appropriate. In some embodiments, even when the control system 112 automatically takes an action as part of the fault reaction state, a fault message 702 may be presented in the display 110 requesting that the physician O acknowledge the action and providing the physician O with the ability to override the action, such as overriding a locking the elongate flexible body 602 into position.

In some embodiments, various types of fault reaction states can be imposed on the flexible robotic system based on the classification of the detected fault. In one example, the fault reaction state can be an Inactive Safe State, which may allow the system to maintain safe servo control of actuators while placing the flexible body 602 in a safe state. For example, the system may detect a fault when the shape sensor is sending faulty data. In this example, the shape sensor may be generating intermittent faults which may not necessitate deactivating actuators but may require verification that the fault is indicative of a system problem. Thus, when the Inactive Safe State is imposed, the response may be to reduce torque to actuator 206 to reduce the effective stiffness of the flexible body 602. The torque can be reduced according to various reduction profiles including a gradual reduction of torque over time along a linear profile or a non-linear profile. Additionally, the response can include maintaining the current position of the catheter by using a position command instead of a torque command. The master assembly 106 can be disabled, meaning the system can ignore any user input commands including control of insertion motion and motion in yaw, pitch, and roll. The Inactive Safe State can include a notification similar to notification 702, which provides an option to clear the detected fault to resume normal operation of the flexible robotic system.

In another example, a detected fault can be classified as a more severe fault imposing an FRL Safe State which places the flexible body 602 in a safe state but prevents motor servo control of actuators. For example, the system may detect a motor fault, encoder fault, or computational fault which can indicate a potentially unsafe condition. Thus, when the FRL Safe State is imposed, the response may be to reduce torque to actuator 206 to reduce the effective stiffness of the flexible body 602. Because the FRL Safe State is imposed in response to a severe fault, the torque may be reduced immediately from a current torque level to zero. Additionally, the response can include removing power from actuators or motors within a manipulator assembly such as manipulator assembly 102. In one example, motor or actuator leads for may be shorted to ground and safety brakes may be applied providing for a breaking effect. In one embodiment, power may be removed from all motors. In an alternative embodiment, severe faults may be further classified into types of severe faults which impose a more specific FRL Safe State associated with a specific motor. The master assembly 106 can be disabled, meaning the system can ignore any user input commands including control of insertion motion and motion in yaw, pitch, and roll. In one example, the detected fault may be classified as recoverable or non-recoverable. For the recoverable fault, the FRL Safe State can include a notification similar to notification 702, which provides an option to clear the detected fault to resume normal operation of the flexible robotic system.

The principles and embodiments of the present disclosure may improve image guided surgery by improving fault handling of a flexible robotic system having a component thereof positioned within a patient during a surgical procedure. Because the appropriate action to take upon detecting a fault may depend upon the fault itself and upon an operational state of the flexible robotic system, a control system is provided to utilize information regarding both the fault and the operational state to identify and enact or impose a fault reaction state to mitigate adverse consequences that may occur due to the fault.

One or more elements in embodiments of the invention, including the method 500 of FIG. 5, may be implemented in software to execute on a processor of a computer system such as control system 112. When implemented in software, the elements of the embodiments of the invention are essentially the code segments to perform the necessary tasks. The program or code segments can be stored in a non-transitory computer-readable storage medium or device, including any medium that can store information including an optical medium, semiconductor medium, and magnetic medium. Computer-readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device. The code segments may be downloaded via computer networks such as the Internet, Intranet, etc. As described herein, operations of accessing, collecting, assigning, detecting, initiating, registered, displaying, receiving, generating, determining, moving data points, segmenting, matching, etc. may be performed at least in part by the control system 112 or the processor thereof. The described embodiments may be combined in various manners within the scope of this disclosure.

Note that the processes and displays presented may not inherently be related to any particular computer or other apparatus. The required structure for a variety of these systems will appear as elements in the claims. In addition, the embodiments of the invention are not described with reference to any particular programming language. It will be appreciated that a variety of programming languages and modalities may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A medical robotic system comprising:
   a manipulator assembly comprising one or more actuators configured to manipulate a flexible elongate body, wherein the one or more actuators comprises a rotation actuator configured to bend a distal end of the flexible elongate body; and
   a control system including one or more processors configured to perform operations, the operations comprising:
   determining an operational state of the medical robotic system;
   detecting a fault in one or more components of the medical robotic system;
   classifying the fault with one or more classifications of a plurality of classifications according to one or more heuristics, wherein the plurality of classifications comprises a motion actuation fault and a non-motion actuation fault; and
   imposing a fault reaction state on the medical robotic system based on the one or more classifications to mitigate the fault, wherein the control system is configured to impose a first fault reaction state when the one or more classifications include the motion actuation fault and to impose a second fault reaction state when the one or more classifications include the non-motion actuation fault, the first fault reaction state being different from the second fault reaction state, wherein imposing the first fault reaction state comprises controlling the rotation actuator to cause the flexible elongate body to become compliant to external forces placed upon the flexible elongate body by walls of an anatomical passageway of a patient.

2. The medical robotic system of claim 1, wherein the one or more components of the medical robotic system includes a shape sensor.

3. The medical robotic system of claim 2, wherein the shape sensor comprises an optical fiber comprising more than one core.

4. The medical robotic system of claim 1, wherein the one or more components of the medical robotic system includes a state sensor within the one or more actuators.

5. The medical robotic system of claim 1, further comprising:
the flexible elongate body, wherein the flexible elongate body comprises a proximal end, a distal end, and a lumen configured to receive a medical instrument; and
a medical instrument detector configured to detect at least one of a presence of the medical instrument within the lumen, a position of the medical instrument relative to the lumen, or a type of the medical instrument.

6. The medical robotic system of claim 5 further comprising a backend housing, wherein:
the flexible elongate body is coupled to the backend housing; and
the backend housing is releasably coupled to the manipulator assembly.

7. The medical robotic system of claim 6, wherein the operational state of the medical robotic system indicates that the backend housing has been manually disengaged from the manipulator assembly.

8. The medical robotic system of one of claim 1, wherein:
the one or more actuators comprises a first insertion actuator configured to move the flexible elongate body along an insertion axis; and
imposing the fault reaction state on the medical robotic system further comprises activating the first insertion actuator to prevent movement of the flexible elongate body along the insertion axis.

9. The medical robotic system of claim 8, wherein imposing the fault reaction state on the medical robotic system further comprises retracting the flexible elongate body by a retraction distance along an insertion axis before activating the first insertion actuator to prevent motion of a medical instrument along the insertion axis.

10. The medical robotic system of claim 5, wherein:
the one or more actuators further comprises a second insertion actuator configured to move the medical instrument along an insertion axis within a lumen of the flexible elongate body; and
imposing the fault reaction state on the medical robotic system further comprises maintaining a shape of the flexible elongate body then retracting the medical instrument by a retraction distance along the insertion axis.

11. A method of control in a medical robotic system, the method comprising:
determining an operational state of the medical robotic system comprising an elongate body having a proximal end, a distal end, and a lumen therebetween;
detecting a fault in one or more components of the medical robotic system;
classifying the fault with one or more classifications of a plurality of classifications according to one or more heuristics, wherein the plurality of classifications comprises a motion actuation fault and a non-motion actuation fault; and
imposing, by one or more processors of a control system, a fault reaction state on the medical robotic system based on the operational state of the medical robotic system and the classification of the fault to mitigate the fault, wherein a first fault reaction state is imposed when the classification of the fault includes the motion actuation fault and a second fault reaction state is imposed when the classification includes the non-motion actuation fault, the first fault reaction state being different from the second fault reaction state, wherein imposing the first fault reaction state comprises controlling actuators, that include one or more rotation actuators configured to bend the distal end of the elongate body, to cause the elongate body to become compliant to external forces placed upon the elongate body by walls of an anatomical passageway of a patient.

12. The method of claim 11, wherein the controlling the actuators includes activating one or more insertion actuators to prevent movement of the elongate body along an insertion axis.

13. The method of claim 11, wherein:
the operational state of the medical robotic system indicates a current configuration of the elongate body, wherein the current configuration of the elongate body includes at least one of a position of the distal end of the elongate body, an orientation of the distal end of the elongate body, or a shape of the elongate body;
the current configuration of the elongate body is based on one or more measurement sensors that include at least two redundant sensors; and
detecting the fault in one or more components of the medical robotic system comprises:
comparing signals from two or more redundant sensors to determine a difference between the signals; and
comparing the difference between the signals to a threshold value.

14. The method of claim 11, wherein:
the operational state of the medical robotic system indicates a current configuration of the elongate body, wherein the current configuration of the elongate body includes at least one of a position of the distal end of the elongate body, an orientation of the distal end of the elongate body, or a shape of the elongate body; and
the current configuration of the elongate body is based on one or more measurement sensors that includes an optical shape sensor comprising a first and second optical core and wherein the fault comprises a detected difference between a first signal received from the first optical core and a second signal received from the second optical core.

15. The method of claim 11, wherein:
the operational state of the medical robotic system indicates a current configuration of the elongate body, wherein the current configuration of the elongate body includes at least one of a position of the distal end of the elongate body, an orientation of the distal end of the elongate body, or a shape of the elongate body;

the current configuration of the elongate body is based on one or more measurement sensors; and detecting the fault in one or more components of the medical robotic system comprises comparing measurements from the one or more measurement sensors to determine a difference between the measurements and comparing the difference between the measurements to a threshold value.

16. The method of claim 11, wherein based on the operational state of the medical robotic system that indicates at least one of: a presence of a medical instrument deployed from the distal end of the elongate body, a position of the medical instrument relative to the lumen, a type of the medical instrument deployed through the elongate body, or that the elongate body is applying a force to a patient anatomy, the control system is configured to:

actively maintain a shape of the elongate body by activating actuators;

initiate a retraction of the medical instrument that includes a needle within the lumen of the elongate body; and control the actuators to cause the elongate body to become compliant to external forces placed upon the elongate body by walls of an anatomical passageway of a patient.

17. The method of claim 11, wherein the detecting the fault in one or more components of the medical robotic system includes detecting that a quality indicator of a registration between the elongate body and a three-dimensional model of one or more anatomical passageways of a patient exceeds an error value.

* * * * *